United States Patent [19]

Hartman

[11] Patent Number: 4,483,781

[45] Date of Patent: Nov. 20, 1984

[54] MAGNESIUM SALTS OF PEROXYCARBOXYLIC ACIDS

[75] Inventor: Frederick A. Hartman, Cincinnati, Ohio

[73] Assignee: The Procter & Gamble Company, Cincinnati, Ohio

[21] Appl. No.: 529,072

[22] Filed: Sep. 2, 1983

[51] Int. Cl.$^3$ .................. C11D 7/38; C11D 7/54; C11D 3/395; C07C 179/10

[52] U.S. Cl. .................. 252/174.12; 252/95; 252/186.25; 252/186.42; 260/502 R

[58] Field of Search ........... 252/95, 186.42, 186.25, 252/174.12; 260/502 R

[56] References Cited

U.S. PATENT DOCUMENTS

| | | |
|---|---|---|
| 2,861,100 | 11/1958 | Humber . |
| 2,957,935 | 10/1960 | Wildl et al. . |
| 3,384,596 | 5/1968 | Moyer . |
| 3,494,786 | 2/1970 | Nielsen .............................. 260/502 R |
| 3,494,787 | 2/1970 | Lund et al. ........................ 260/502R |
| 3,639,285 | 2/1972 | Nielsen . |
| 3,770,816 | 11/1973 | Nielsen . |
| 4,094,808 | 6/1978 | Stewart et al. . |
| 4,126,573 | 11/1978 | Johnston ..................... 260/502 R |
| 4,154,695 | 5/1979 | McCrudden et al. ........... 260/502 R |
| 4,170,453 | 10/1979 | Kitko .............................. 260/502 R |
| 4,225,451 | 9/1980 | McCrudden et al. . |
| 4,287,135 | 9/1981 | Stober et al. . |
| 4,288,388 | 9/1981 | McCrudden et al. . |
| 4,385,008 | 5/1983 | Hignett .............................. 562/492 |
| 4,403,994 | 9/1983 | Hignett .......................... 260/502 R |

FOREIGN PATENT DOCUMENTS

| | | |
|---|---|---|
| 0027893 | 4/1981 | European Pat. Off. . |
| 0066992 | 12/1982 | European Pat. Off. ........ 260/502 R |

*Primary Examiner*—Mary F. Downey
*Assistant Examiner*—Mukund J. Shah
*Attorney, Agent, or Firm*—Robert B. Aylor; Richard C. Witte; Thomas H. O'Flaherty

[57] ABSTRACT

The present invention relates to solid magnesium peroxycarboxylate salts and detergent compositions containing them. These compounds have markedly improved stability characteristics relative to the corresponding peroxycarboxylic acids, especially when admixed with alkaline granular detergent products. The activity of the magnesium peroxycarboxylate salts after dissolution is the same as that of the corresponding peroxycarboxylic acids, especially when used as laundry bleaches. The compound within this invention also have improved odor and dissolution characteristics relative to the corresponding peroxycarboxylic acids.

20 Claims, No Drawings

MAGNESIUM SALTS OF PEROXYCARBOXYLIC ACIDS

TECHNICAL FIELD

This application relates to stable solid peroxycarboxylates.

BACKGROUND ART

There have been numerous attempts to enhance the storage stability of peroxycarboxylic acids. It is well known to enhance the storage stability of peroxycarboxylic acids by encapsulating or coating them. U.S. Pat. No. 4,288,388, McCrudden et al (Sept. 8, 1981), discloses aromatic peroxycarboxylic acids compounds containing at least three peroxycarboxylic acid groups. It is stated that such compounds can be desensitized by admixing, granulating or coating them with a diluent such as magnesium sulfate. Desensitizing is reducing the explosiveness of the compounds.

U.S. Pat. No. 4,287,135, Stober et al (Sept. 1, 1981), discloses that diperoxyalkanedioic acids and aromatic peroxycarboxylic acids can be prepared by reacting a dialkanoic acid or an aromatic carboxylic acid with hydrogen peroxide and sulfuric acid and then producing a desensitizing agent for the peroxycarboxylic acid in situ by adding alkali metal hydroxide, alkali metal aluminate or an alkaline earth metal hydroxide so that the filtrate is free of sulfuric acid. It is stated that the resulting salt coats the peracid and thus the product is desensitized and stable in storage.

U.S. Pat. No. 4,094,808, Stewart et al (June 13, 1978), discloses an organic peroxycarboxylic acid formulation in the form of an encapsulated core comprising particles of a solid organic peroxycarboxylic acid in admixture with particles of a material substantially more water-soluble than the organic peroxycarboxylic acid that is utilized as a dispersing agent. The core is completely encapsulated with a hydratable inorganic salt in less than the maximum state of hydration; for example, $MgSO_4 \cdot H_2O$.

U.S. Pat. No. 3,639,285, Nielsen (Feb. 1, 1972), discloses that the stability of monoperoxyphthalic acids or diperoxyphthalic acids and mixtures thereof can be substantially improved by incorporating therewith an alkali metal or an alkaline earth metal salt of an acid having an ionization constant of the first hydrogen at 25° C. of at least $1 \times 10^{-3}$; for example, magnesium sulfate.

It is known that the magnesium salt of a carboxylic acid containing a peroxycarboxylic acid group is stable. U.S. Pat. No. 4,385,008, Hignet (May 24, 1983), discloses in solid form the magnesium salt of certain aromatic, cycloaliphatic or conjugated aliphatic compounds containing a peroxycarboxylic acid group and a carboxylate group. It is clearly pointed out that the magnesium salt formed is that of the carboxylic acid group only and that the peroxycarboxyl group remains in acid form. It is stated that such compounds have excellent storage stability.

Some salts of peroxycarboxylic acids in solid form are known. U.S. Pat. No. 2,957,935, Wildl et al (Oct. 25, 1960), discloses a process to prepare mercury peroxycarboxylates.

U.S. Pat. No. 2,861,100, Humber (Nov. 18, 1958), discloses a process of the preparation and isolation of the anhydrous salts of a saturated aliphatic peroxycarboxylic acid.

German Pat. No. 1,099,538, D'Ans et al (published Feb. 16, 1961), discloses a process for the production of anhydrous, solid or dissolved, alkali metal or alkaline earth salts of organic hydroperoxides. See also: J. D'Ans and H. Gold, Chem. Ber., 92, 2559 (1959).

U.S. Pat. No. 3,384,596, Moyer (May 21, 1968) and British Pat. No. 1,222,437, Moyer (Apr. 16, 1968) discloses an aqueous bleaching composition of 3-chloroperoxybenzoic acid having a pH of at least 9 with either calcium or magnesium ion employed at a ratio to the peroxycarboxylic acid of 0.5 to 1.0 is improved bleaching activity over similar aqueous bleaching compositions which lack the calcium or magnesium ions. It is alleged that the effect is not due to stabilization (Col. 2, lines 61-66).

U.S. Pat. No. 3,494,787, Lund and Nielsen (Feb. 10, 1970) discloses storage stable diperoxyphthalic acids encapsulated in a protective coating of a hydrated salt such as magnesium sulfate. It is clearly pointed out that the particles so formed consist of a core of diperoxyphthalic acid bleaching agent surrounded by a layer or shell of inorganic, hydrated, water soluble salt.

U.S. Pat. No. 3,494,786, Nielson (Feb. 10, 1970) discloses granulated compositions of peroxyphthalic acid cores encapsulated in protective coatings of hydrated magnesium sulfate.

U.S. Pat. No. 3,510,512, Jourdan-Laforte (May 5, 1970) discloses a method for obtaining stable monoperoxyphthalic acid from the reaction of phthalic anhydride and hydrogen peroxide in a halogenated hydrocarbon solvent with an alkaline catalyst.

U.S. Pat. No. 3,235,584, Blumbergs (Feb. 15, 1966) discloses a process for producing peroxycarboxylic acids from organic acid halides and aqueous alkaline hydrogen peroxide solutions. Either alkali metal peroxides or alkaline earth metal peroxides are used to form aqueous solutions of the alkali metal or alkaline earth metal salt of the peroxycarboxylic acid. The salts are acidified to form the peroxycarboxylic acid.

U.S. Pat. No. 4,321,301, Brichard and Colery (Mar. 23, 1982) discloses a process for stabilizing particles of peroxygenated compounds, including peroxycarboxylic acids, by coating with a boron compound. These particles are said to lose less than 15% active oxygen after two weeks when admixed with base detergent powder.

U.S. Pat. No. 3,847,830, Williams et al (Nov. 12, 1974) discloses a peroxygen containing composition enveloped in a water dispersible layer for improved storage stability. Suitable water dispersible layers are composed of fatty acids, glycerol esters, and alkanolamide derivatives.

European Patent Application No. 0030759, Brichard (published Mar. 12, 1980) discloses a process for stabilizing peroxygen containing particles, including peroxycarboxylic acids, by coating them in a fluid bed with waxes such as fatty acid esters and amides, polyethyleneglycol, glycerol, alcohols, and various polymers.

U.S. Pat. No. 2,838,459, Sprout (June 10, 1958) discloses the stabilization of solutions containing peroxygen compounds using a stabilizer additive which liberates magnesium ions in alkaline aqueous solutions. For example, magnesium sulfate, chloride, and silicate may be used.

U.S. Pat. No. 4,128,495, McCrudden (Dec. 5, 1970) discloses bleaching compositions of phthaloyl peroxides which are desensitized by intimate contact with a diluent, e.g., magnesium sulfate.

Japanese Kokai Tokkyo Koho No. 80 445,654, Application No. 78/119,481, Takao et al (Mar. 31, 1980) discloses the stabilization of liquid peroxycarboxylic acids with thiocyanate salts, e.g., sodium, potassium, ammonium, or magnesium thiocyanate.

U.S. Pat. No. 2,670,266 (Feb. 23, 1954) discloses alkali metal persalts useful as bleaching agents.

British Patent No. 656,938 (Sept. 5, 1951) discloses salts of peroxycarboxylic acids which are useful in shrinkproofing wool.

European Patent Application No. 74,730, Millar (published Mar. 23, 1983) discloses a method for granulating magnesium salts of various peroxycarboxylic acid carboxylates described in European Patent application No. 27693 (U.S. Pat. No. 4,385,008, Hignet, May 24, 1983).

Belgian Patent No. 560,389 (Sept. 3, 1956) discloses a stabilized mixture of organic peroxycarboxylic acid and mineral salts capable of absorbing water as water of crystallization.

Masao Ōkubo et al, *Bull. Chem. Soc. Jap.*, 44, 1365-1368 (1971) discloses a complex containing magnesium, bromine, and benzoyl peroxide.

Additional disclosures include G. Sosnovsky and J. Brown, *Chem. Rev.*, 66, 329 (1966) and G. A. Razuvaev et al in "Organic Peroxides", Vol. 111, D. Swern, Ed., Wiley-Interscience, New York (1978), Ch. 3, p. 141.

All of the above patents and literature are incorporated herein by reference.

SUMMARY OF THE INVENTION

This invention relates to magnesium peroxycarboxylates in solid form and their use, e.g., in detergent compositions.

Any organic compound comprising the group

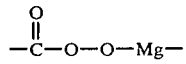

is more stable than the corresponding compound comprising the group

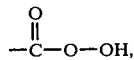

especially if the aforementioned groups contain some degree of hydration. In the solid form, the association between peroxycarboxylate and magnesium can be partly due to covalent bonding and partly due to ionic bonding. This relationship is common in salts of weak acids such as peroxycarboxylic acids. The relative contribution of each type of bonding is determined in part by the acidity of the peroxycarboxylic acid, which varies according to the structure of the peroxycarboxylic acid. Relatively acidic peroxycarboxylic acids will exhibit more of an ionic bond to magnesium than less acidic peroxycarboxylic acids. The structure

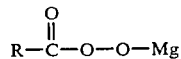

depicts this arrangement generically by the dash between O and Mg. In actual fact, the geometric arrangement of atoms can include examples where O and Mg are quite far apart in the molecular structure. However, the inherent association between the peroxycarboxylate moiety and the Mg is believed to be essential.

The magnesium peroxycarboxylates can be represented by the general formula:

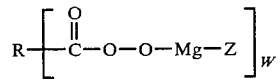

wherein R is hydrogen (H), oxygen (O-), or an organic moiety hereinafter defined, Z is a counterion hereinafter defined and W is hereinafter defined. Such solid compounds possess excellent storage stability both alone and when mixed with additional solid components. Such additional solid components can even be alkaline. Stability, as used herein, means that the active oxygen contained in the magnesium peroxycarboxylates is retained during storage to a much greater extent than is the active oxygen contained in the corresponding peroxycarboxylic acids. The active oxygen contained in the solid magnesium peroxycarboxylates is generally readily available. This means that the solid magnesium peroxycarboxylates are readily soluble or dispersible and yield solutions containing active oxygen. When the solution is aqueous, it cannot be distinguished from an aqueous solution prepared from the corresponding peroxycarboxylic acid, and an equivalent amount of magnesium, when the compared solutions are adjusted to the same pH.

The utility of the magnesium peroxycarboxylate is generally not diminished relative to that of the corresponding peroxycarboxylic acid. For example, the magnesium peroxycarboxylates can be used as bleaching agents, oxidizing agents, epoxidizing agents, polymerization initiators, dehydrogenating agents, herbicides, and germicides. In general, the solid magnesium peroxycarboxylates can be substituted for the corresponding peroxycarboxylic acids for any purpose. Additionally, it will be shown that the solid magnesium peroxycarboxylates are preferred over the corresponding peroxycarboxylic acids for many uses. This preference is partly due to the superior stability of the solid magnesium peroxycarboxylates and partly due to the increased safety to the substrate. Also, the solid magnesium peroxycarboxylates also have superior odor, dispersability, and handling properties relative to the corresponding peroxycarboxylic acids.

Also, in many cases the peroxycarboxylate form is the desired reactant. Normally, this is generated by adding alkalinity to a solution of the corresponding peroxycarboxylic acid. This usually results in some decomposition of the peroxycarboxylic acid [Akiba and Simamura, *Tetrahedron*, 26, 2519 (1970)]. If the percarboxylic acid form is preferred, it can be generated easily by adding acidity to a solution of the corresponding magnesium peroxycarboxylate salt, a process which does not generally result in significant decomposition. [Goodman et al, *Trans. Farad. Soc.*, 58, 1846 (1962).]

The lack of a noticeable odor simplifies the perfuming of products containing these magnesium peroxycarboxylates. There is no need to add components simply to cover the odor. However, it is desirable to avoid bleach-reactive perfume ingredients if they can contact the peroxycarboxylate.

Specific applications of the solid magnesium peroxycarboxylates include use in laundry detergents and additives as bleaches and disinfectants, in toilet bowl cleansers, automatic dishwashing powders, hard surface cleaners, denture cleansers, hair bleaching products, acne creams, and in industrial oxidations.

DETAILED DESCRIPTION OF THE INVENTION

The present invention is based primarily upon the discovery that solid magnesium peroxycarboxylates possess excellent storage stability both alone and admixed with other compounds. This is surprising because peroxycarboxylic acids are generally unstable in that they readily lose their active oxygen. The active oxygen is defined as the oxygen contained in a molecule which is easily transferred via a chemical reaction to another compound. A peroxycarboxylic acid which has lost its active oxygen is usually simply a carboxylic acid. Peroxycarboxylic acids are even more unstable when admixed with other compounds. It is believed that these other compounds, especially alkaline compounds, hydrolyze the peroxycarboxylic acids to produce hydrogen peroxide which is particularly unstable and quickly loses its active oxygen. Additionally, the influence of transition metal impurities in such other compounds is known to be deleterious to the stability of peroxycarboxylic acids. Heat also destabilizes peroxycarboxylic acids.

Essentially any magnesium peroxycarboxylate provides improved storage stability as compared to the corresponding peroxycarboxylic acid. The choice of solid magnesium peroxycarboxylate is dependent only on its desired end use. However, it should be noted that some solid peroxycarboxylates are more stable than others. This is related to the fact that some peroxycarboxylic acids are more stable than others. Therefore, the solid magnesium peroxycarboxylates are correspondingly more stable if formed from a more stable peroxycarboxylic acid. Those peroxycarboxylic acids which have higher molecular weights are usually more stable. Also, aromatic peroxycarboxylic acids having the substituents disclosed in U.S. Pat. No. 3,075,921, Brocklehurst and Pengilly (Jan. 29, 1963) are more stable. Said patent is incorporated by reference.

Other suitable aromatic peroxycarboxylic acids are disclosed in U.S. Pat. No. 4,221,660, Eggonspenger et al (Sept. 9, 1980), incorporated herein by reference.

Fatty peroxycarboxylic acids having more than 12 carbon atoms are more stable at temperatures above 50° C. than shorter peroxycarboxylic acids, since they remain solid at such temperatures. Preferably, the fatty peroxycarboxylic acids contain more than about 8 carbon atoms for stability reasons. Substituted fatty peroxycarboxylic acids with melting points above about 50° C. are preferred.

The preferred hydrated solid magnesium peroxycarboxylates have the general formula:

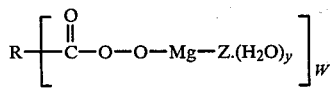

wherein R is H or an organic moiety, Z is a negatively charged organic or inorganic moiety, Y is from about 0 to about 6, preferably from about 1 to about 6, and W is from about 1 to 3.

Preferably R is selected from the group consisting of linear or branched alkyl groups containing from about 1 to about 20 carbon atoms (more preferably from about 8 to about 18), an aryl group, an aromatic heterocyclic group, a polyarylene group consisting of from about 2 to about 4 annelated benzenoid rings, and mixtures thereof. Also, R can be substituted with essentially any group or groups including hydroxy, halogen (chloro, bromo, or fluoro), sulfonate, nitro, carboxylate, phenyl, $C_{4-5}$ alkoxy (e.g. ethoxy), hydroxy sulfonyl, aryl, heteroaryl, sulfone, amine oxide, ammonium and substituted ammonium ($R_4{}^1N+$, wherein $R^1$ is hereinafter defined), amide, ester, nitrile, and sulfate groups to replace a hydrogen atom attached to the alkyl or aryl portions of the R moiety. R may not contain substituents which would react readily with the active oxygen from the percarboxylate groups. Such reactive groups may include electrophilic groups such as ketones, sulfoxides, reactive esters or $\alpha,-\beta$-unsaturated carbonyls, nitriles, etc. Preferably, the peroxycarboxylic acid has a melting point above about 50° C., most preferably above about 60° C.

The R group may be covalently bonded to other R groups to form a polymer. Typically, R in this case is an alkylene, e.g., vinyl, group substituted with the magnesium peroxycarboxylate. Usually the number of repeating R groups, m, averages from about 2 to about 100.

For example, the polymer can have the formula:

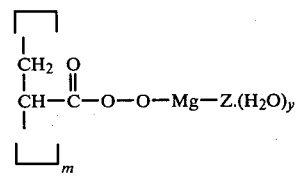

wherein m is from about 2 to about 100, Z is as defined hereinbefore, and y is from 0 to 6, preferably at least about 1. The terminal groups on the polymer which is composed of repeating R groups may be H, —OCH$_3$, or any group resulting from a quenching compound used in polymerization reactions. Any of the substituents hereinabove defined may be used to replace one or more of the hydrogen atoms attached to the repeating vinyl units.

It is preferred that y be about 4. This is based on the analysis of the solid magnesium peroxycarboxylates prepared as described hereinafter which shows that the tetrahydrate is formed. Storage data described hereinafter show that some degree of hydration is important to maintenance of the desirable stability of the solid magnesium peroxycarboxylates. However, the exact level of hydration is not believed to be essential.

It is preferred that Z have the general formula:

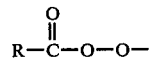

wherein R is defined above. Such a selection of Z is preferred because twice as much active oxygen per mole of magnesium is present than in examples where Z contains no active oxygen. R and Z can be covalently bonded, as in the case of a diperoxycarboxylic acid. However, Z can also be a corresponding carboxylate, sulfate, sulfonate, chloride, bromide, nitrate, etc. anion. The anion obviously should be one that is not readily oxidized by the peroxycarboxylate.

The more preferred R groups consist of branched and linear alkyl groups containing at least 8 carbon atoms preferably from about 8 to about 14 carbon atoms or a substituted aryl group of the types shown below:

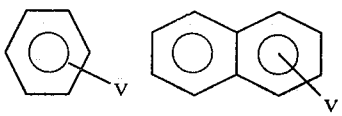

where each V is a substituent selected from the group including $NH_3^+$, $NR_3^+$, F, Cl, Br, $-SO_3-M^+$, $-CO_2^-M^+$, $-NO_2$, $-OCH_3$, $-CH_3$, $-CF_3$, $-C\equiv N$ and H where M is an alkali or alkaline earth metal.

The most preferred R groups are as follows:

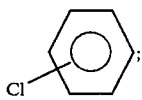

n—$C_{11}H_{23}$—; —$(CH_2)_{10}$—; and n-$C_{10}H_{23}$CH—; and n-$C_{10}H_{21}$'—CH—
     |                         |
     Cl                       $CH_2$—

The most preferred Z groups are:

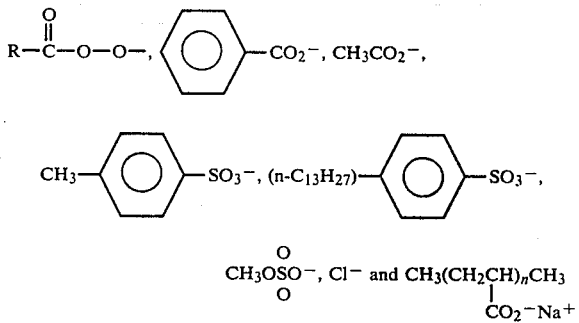

where n is approximately 50.

It is believed that the increased stability of the magnesium peroxycarboxylates relative to the corresponding peroxycarboxylic acids arises from two primary considerations. The active oxygen atom within the peroxycarboxylic acids is known to be electrophilic in nature (V. G. Dryuk, *Tetrahedron*, 32, 2855 [1976]). As such, it is readily attacked by nucleophilic agents resulting in loss of the active oxygen. Such nucleophilic agents are common in, for example, detergent compositions.

In the corresponding peroxycarboxylate, the active oxygen atom is known to be nucleophilic [(J. E. McIsaac, Jr. et al, *J. Org. Chem.*, 37, 1037 (1972)]. Electrophilic agents are much less common in, e.g., detergent compositions. These factors are also discussed in F. Fulira and G. Modena, *Pure and Appl. Chem.*, 54, 1853 (1982).

Unfortunately, many peroxycarboxylates are unstable. For example, sodium peroxyacetate is so unstable as to be explosive (L. G. Humber, J. Org. Chem., 24, 1789 [1959]). Mercuric peroxybenzoate is apparently stable alone in a moist state but is unstable when dried out (U.S. Pat. No. 2,957,935, 1956). Sodium peroxybenzoate is unstable [B. T. Brooks and W. D. Brooks, *J. Am. Chem. Soc.*, 55, 4309 (1933)]. Even solutions of some peroxycarboxylates are unstable [F. P. Greenspan et al, *J. Org. Chem.*, 20, 215 (1955)]. We have found that only the magnesium peroxycarboxylates are stable to a useful degree. This may be because of the ability of the magnesium cation to maintain a degree of hydration, which promotes the stability of the peroxycarboxylate (U.S. Pat. No. 4,385,008, Hignett, 1983, incorporated herein by reference). The stabilizing influence of the hydrated magnesium counterion on the already stable peroxycarboxylate is believed to be important to achieving the desirably high level of storage stability of these compounds.

The compounds within the invention are prepared via the following process. An aqueous suspension or solution of a magnesium salt in which the anion is the conjugate base of a weak acid having a $pK_a$ of greater than about 6 is formed. To such an aqueous suspension or solution is added a peroxycarboxylic acid of the general formula:

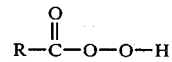

wherein R is as defined hereinbefore. The level of magnesium from the magnesium salt and the amount of peroxycarboxylic acid utilized in such solution or suspension is such that the molar ratio of magnesium:-peroxycarboxylic acid is from about 10 to about 0.1, preferably from about 3 to about 1, and most preferably about 2. A ratio of about 2 is most preferred because essentially all of the magnesium and peroxycarboxylic acid can interact and essentially none of each compound is wasted.

It is essential that the peroxycarboxylic acid be partially or completely miscible with the aqueous solution or suspension. Therefore, if the peroxycarboxylic acid is not inherently miscible with the aqueous suspension or solution, it can be solubilized in the following manner. The peroxycarboxylic acid can be predissolved in an organic cosolvent. Preferred organic cosolvents are partially or completely miscible with water. While the physical characteristics of solvents of this type are complex, many such cosolvents have a dielectric constant from about 5 to about 50 and include sites available for hydrogen bonding with water. The more preferred solvents are ethyl acetate, t-butyl alcohol, methanol, tetrahydrofuran, tetrahydropyran, and ethanol and mixtures thereof, with ethyl acetate and t-butyl alcohol being most preferred. Non-miscible solvents, such as chloroform or dichloromethane, do not solubilize the peroxycarboxylic acid in the aqueous suspension or solution and, consequently, do not allow effective interaction between the magnesium salt and peroxycarboxylic acid with subsequent formation of the magnesium peroxycarboxylate. Some organic solvents are not preferred because they can react with the peroxyacid. This group includes dimethyl sulfoxide, carbon disulfide, and solvents which contain multiple bonds. Also, it is desirable that the organic cosolvent selected not solubilize the magnesium peroxycarboxylate product to a significant extent. This will facilitate the isolation of the product as a solid precipitate.

The addition of the peroxycarboxylic acid to the solution or suspension of the magnesium salt results in the formation of a precipitate. It is believed that the precipitate formed is one of the compounds within the invention. The precipitate can be separated by any standard technique. For example, filtration, decantation, and/or centrifugation can be used. The precipitate can then be washed with water, and, if used, the organic cosolvent, to remove any unreacted starting materials. Finally, the precipitate is dried to remove any water in excess of the hydration discussed above. This can be effected by any standard means of drying. For example, vacuum dessication, mild heating at ambient pressure, or air drying can be used.

In the preferred embodiment the process is carried out as follows. A magnesium salt with the general formula;

Mg—X wherein X is a suitable counterion, or counterions, that renders the magnesium salt water soluble or dispersible, and a hydroxide compound with the general formula:

Y—OH wherein Y is a suitable counterion that renders the hydroxide compound water-soluble, are placed in aqueous solution. Preferably, X is selected from the group consisting of $(NO_3^-)_2$, $SO_4^{-2}$, and $(CH_3COO^-)_2$ and Y is selected from the group consisting of alkali metals, ammonium, and substituted ammonium, phosphonium, or sulfonium cations, e.g., of the type $R_4^1N^+$ where $R^1$ is a linear or branched alkyl or alkylene group containing from 1 to about 5 carbon atoms. The most preferred X is $SO_4^{-2}$ and the most preferred Y is sodium. Such compounds react to form a colloidal suspension of $Mg(OH)_2$ and a water soluble salt which is $Na_2SO_4$ in the most preferred example. Such a reaction can be presented by the following general formula:

$$MgX + Y-OH \div Mg(OH)_2(sus) + X^+ + Y^-$$

wherein X and Y are defined hereinabove.

It is believed that the formation of the colloidally suspended $Mg(OH)_2$ is preferred for the process. This is based upon the fact that direct addition of $Mg(OH)_2$ to the reaction solution results in an excessively slow rate of reaction between the $Mg(OH)_2$ and the peroxycarboxylic acid subsequently added to the aqueous solution. This slower rate of reaction is thought to be due to the limited surface area available for reaction on the directly added $Mg(OH)_2$ relative to that for the colloidal $Mg(OH)_2$ which is formed in situ as described hereinabove.

In an alternate embodiment, the peroxycarboxylic acid can be formed in situ. This eliminates the necessity of having to handle peroxyacids in the pure or nearly pure form in which they may be unstable. For example, the peroxycarboxylic acid can be formed from the corresponding carboxylic acid by oxidizing the carboxylic acid in a solution of sulfuric or methanesulfonic acids using hydrogen peroxide after the method described in U.S. Pat. No. 4,377,213, incorporated herein by reference. The peroxycarboxylic acid produced by this reaction can then be extracted with an organic solvent such as ethyl acetate or t-butyl alcohol. The solution of the peroxycarboxylic acid in the organic solvent can then be introduced to the $Mg(OH)_2$ aqueous suspension formed as described above. The isolation of the product magnesium peroxycarboxylate then follows the general procedure described above.

Also, peroxycarboxylic acids can be formed from the corresponding acyl halide or anhydride after the method described in U.S. Pat. No. 3,485,869, MacKeilar et al, incorporated herein by reference. The peroxycarboxylic acid in this case is prepared via a reaction of the acyl halide or anhydride with alkaline hydrogen peroxide. The resulting reaction mixture containing the peroxycarboxylic acid can then be added directly to the $Mg(OH)_2$ aqueous suspension described above. Alternatively, the reaction mixture can be acidified and the alcoholic peroxycarboxylic acid solution can be added to an aqueous suspension of magnesium hydroxide. Other methods for producing peroxycarboxylic acids are known and it is believed that, in any of them, complete isolation and purification is not essential prior to forming the magnesium peroxycarboxylate.

The precipitate formed from the reaction between the magnesium salt and peroxycarboxylic acid described hereinbefore is initially a wet solid. It is believed to be desirable under some circumstances, e.g., when the peroxycarboxylic acid is relatively insoluble, to add to this wet amorphous solid other agents which can help disperse the product once dried or to help to maintain the state of hydration or for any other reason. The addition of these other agents can be conveniently effected at this stage of the process before the solid magnesium peroxycarboxylate is dried as hereinbefore described. Examples of such additives include polymers of acrylic acid and its neutralized salts having a molecular weight maximum of between 500 and 80,000. These polymers of acrylic acid or its neutralized salts can be added as an aqueous solution or suspension or as a solid which is intermixed with the wet product magnesium peroxycarboxylate. Other additives can be selected from the group consisting of 4-toluenesulfonic acid or its sodium salt, polyvinylpyrrolidone, polystyrene sulfonate, polyethylene glycols, sodium sulfate, magnesium salts of weak acids having $pK_a$ values of between about 3.5 and about 5.5 and detergent surfactant molecules selected from the group which includes linear alkylbenzene sulfonates, alcohol sulfates, linear alkyl ethoxylates, alkyl glycosides, and mixtures thereof. The preferred alkyl chain length in those detergent surfactants is from about 10 to about 18 carbon atoms.

The products are obtained after the drying steps described hereinbefore are typically in the form of fine powders. It is often desirable to increase the particle size of these products so as to control dustiness or prevent or reduce the amount of segregation that occurs when the product is admixed with larger compounds having other particle sizes. The products of the process described hereinbefore which are thought to be magnesium peroxycarboxylates can be agglomerated or extruded to increase their particle size to a desirable level. Such processes are typically found not to impair the desirable stability characteristics of these products. In addition, increased particle sizes are believed to increase the volume to surface area ratio. This can reduce the relative amount of the magnesium peroxycarboxylate which can be exposed to any external hostile environment. Increased particle sizes are found in many cases to actually increase the stability of the magnesium peroxycarboxylates, particularly when said magnesium peroxycarboxylates are admixed with other compounds which are hostile to the stability of the corresponding peroxycarboxylic acid.

The detergent compositions of this invention comprise from about 0.01% to about 99% of a detergent surfactant, detergent builder or mixtures thereof and from about 0.001% to about 80% of the stable magnesium peroxycarboxylates of this invention. Preferably the compositions contain from about 5% to about 25% detergent surfactant, from about 15% to about 50% detergent builder, and from about 0.1% to about 10% magnesium peroxycarboxylate to give from about 0.005% to about 0.5% available oxygen.

Suitable detergent compositions and detergent ingredients are disclosed in U.S. Pat. Nos. 4,166,039, Wise; 4,157,978, Llenado; 4,056,481, Tate; 4,049,586, Collier; 4,035,257, Cherney; 4,019,998, Benson et al; 4,000,080, Bartolotta et al; and 3,983,078, Collins, all of which are incorporated herein by reference. Other disclosures of additional ingredients appear in U.S. Pat. Nos. 4,089,945, 3,987,161; and 3,962,418, incorporated herein by reference. Preferably, the compositions are in solid granular or particulate form and preferably are substantially free of compounds that will or can react with the active oxygen in the magnesium peroxycarboxylate.

The bleach compositions of this invention comprise from 0% to about 50% detergent surfactant, detergent builder, or mixtures thereof and from about 1% to 100% of the stable magnesium peroxycarboxylates of this invention. Preferably, the compositions contain from about 1% to 15% detergent surfactant, from about 5% to 50% detergent builder, from about 5% to 65% inorganic salts, and from about 3% to 25% magnesium peroxycarboxylates to give from about 0.015% to about 0.125% active oxygen.

Suitable bleach compositions and additional compositions are disclosed in U.S. Pat. Nos. 4,329,245 Eymond and Butterworth (May 11, 1982), 4,254,201, Cockrell and Hanley (Mar. 31, 1981), 4,325,828, Postlethwaite (Apr. 20, 1982), 4,374,035, Bossu (Feb. 15, 1983), 3,789,000, Berkowitz (Jan. 29, 1974), with the magnesium peroxycarboxylates substituted for the active oxygen or chlorine components cited, all of said patents being incorporated herein by reference.

The solid magnesium peroxycarboxylates of this invention and their solutions are useful in carrying out oxidations of various materials to prepare more useful products. Such oxidations which are particularly applicable are those wherein the initial stage of the oxidation involves a nucleophilic attack by the peroxycarboxylate anion, for example, on the carbonyl carbon of a ketone to generate an ester, or on the sulfinyl sulfur of a sulfoxide to generate a sulfone [Curci et al, *Tetrahedron*, 22, 1235 (1966), Ogata and Sawaki, *J. Am. Chem. Soc.*, 94, 4189 (1972), and Robson, *J. Chem. Soc.*, 5170 (1964).] In these reactions, the need to add alkalinity to a peroxycarboxylic acid solution is avoided. In oxidations where the peroxycarboxylic acid is preferred, for example, epoxidations, the magnesium percarboxylate solutions can be acidified to generate the peroxycarboxylic acid.

As used herein all parts, percentages and ratios are by weight unless otherwise specified.

The following examples illustrate the invention.

EXAMPLE 1

Preparation of Magnesium bis(3-chloroperoxybenzoate)tetrahydrate

A solution of magnesium sulfate (3.25 g, 27.0 mmol) in water (50 mL) was adjusted to pH 10.0 with an aqueous sodium hydroxide solution (10.0 mL of 2.7 M, 27.0 mmol) to give a colloidal suspension of magnesium hydroxide. 3-Chloroperoxybenzoic acid (98%, 9.51 g, 54.0 mmol) dissolved in ethyl acetate (60 mL) was added all at once with vigorous stirring. After 5 min, the wet precipitate was collected by filtration, washed with water (ca. 100 mL), and allowed to dry overnight giving 4.83 g (41% yield based on $Mg^{2+}$, 49% active oxygen retained) of a fine colorless powder: Analysis Calculated (Anal. Calcd) for $C_{14}H_{16}Cl_2MgO_{10}$: C, 38.26; H, 3.67; Cl, 16.13; Mg, 5.53; O(active), 7.28. Found: C, 38.15; H, 3.71; Cl, 15.75; Mg, 5.93; O(active) 6.93; S, 0.87.

EXAMPLE 2

Alternate Preparation of Magnesium bis(3-chloroperoxybenzoate)tetrahydrate

The procedure of Example 1 was reproduced exactly except that the levels of magnesium sulfate and 3-chloroperoxybenzoic acid used were decreased by half. This gave the intermediate colloidal solution of magnesium hydroxide at pH 11.1. The process gave 4.25 g (71.7% based in $Mg^{2+}$, 70.0% active oxygen retained) of a fine white colorless powder: Found: C, 39.10; H, 3.82; Cl, 16.60; Mg, 5.55; O(active), 6.85.

COMPARATIVE EXAMPLE 2a

Attempted Preparation of Peroxycarboxylate Salts of Zinc, Cadmium, Mercury, Aluminum, and Lithium The procedure described in Example 2 was followed exactly except that magnesium sulfate was replaced in each of five experiments by equivalent amounts of zinc, calcium, mercuric, aluminum, and lithium sulfates. The results of these experiments are described in the following table:

| Metal | Yield (based on the metal ion) | % active oxygen (days) |
|---|---|---|
| Zn | 21 | 1.76(0) 2.59(1) 2.21(2) 2.02(3) 1.71(6) |
| Ca | 15 | 0.18(0) 0.10(1) |
| Al | 12 | 1.53(0) 1.44(1) 1.13(2) 1.18(6) |
| Hg | 0 | 0.00 |
| Li | 0 | (NA) |

It should be noted that this procedure is not optimized for preparing these metal peroxycarboxylates. Other methods discussed later give better results. With mercuric sulfate, only a small amount of product was obtained by filtration. It was yellowish brown and contained virtually no active oxygen. With lithium sulfate, as expected, the peroxycarboxylate which probably was formed was soluble in the reaction medium. The increase in active oxygen percentage for zinc bis(peroxycarboxylate) after one day may be attributed to loss of moisture by evaporation.

EXAMPLE 3

Preparation of Magnesium bis(peroxydodecanoate)tetrahydrate

A solution of magnesium sulfate (3.25 g, 27.0 mmol) in water (50 mL) was adjusted with an aqueous sodium hydroxide solution (10.5 mL of 3.9 M, 41 mmol) to give a colloidal suspension of magnesium hydroxide. Peroxydodecanoic acid (91.9%, 12.7 g, 54.0 mmol) dissolved in ethyl acetate (60 mL) was added all at once with vigorous stirring. After 5 min, the wet precipitate was collected by filtration, washed with ethyl acetate (ca. 50 mL) and water (ca. 100 mL) and allowed to dry overnight giving 4.65 g (32.7% based on $Mg^{2+}$, 29% active oxygen retained) of a fine white powder: mp 140°–145° C.(dec); Anal. Calcd for: $C_{24}H_{54}MgO_{10}$: C, 54.69; H, 10.32; Mg, 4.61; O(active), 6.07. Found: C, 55.21; H, 10.19; Mg, 4.96; O(active), 5.35.

EXAMPLE 4

Preparation of Magnesium Benzoate 4-Chloroperoxybenzoate Tetrahydrate

Magnesium oxide (0.443 g, 11.0 mmol) was added to a solution of 4-chloroperoxybenzoic acid (94.6%, 2.00 g, 11.0 mmol) and benzoic acid (1.26 g, 10.3 mmol) in 65 mL of ethyl acetate and 0.80 mL of water. After 90 min of vigorous stirring, the precipitate was collected via filtration, washed with ethyl acetate (ca. 50 mL), and vacuum dried to give 3.50 g (82% based on $Mg^{2+}$) of a white powder: Anal. Calcd for $C_{14}H_{17}ClMgO_9$: C, 43.22; H, 4.40; Cl, 9.11; Mg, 6.25; O(active), 4.11. Found: C, 43.88; H, 4.07; Cl, 9.79; Mg, 6.80; O(active), 3.95.

EXAMPLE 5

Preparation of Magnesium bis(peroxylaurate) Admixed with Alkyl Glycosides

The procedure outlined in Example 3 was reproduced exactly except that the wet precipitate collected by filtration was divided into two fractions. Separately, a sample of crude alkyl polyglycosides having a $C_{12}$ alkyl group and an average of 1.7 glycoside units was dissolved in 0.1 N sodium hydroxide solution to which ethylenediaminetetraacetate (EDTA) was added (25% w/w). The aqueous portion was allowed to evaporate over a 3 day period giving a wet crystalline mass. This mass was added to a 30% aqueous solution of hydrogen peroxide which was allowed to stand overnight. This ca. 100 mL solution was added all at once to 2 L of acetone. The purified alkyl glycosides precipitated. The precipitate was collected via filtration, washed in acetone (2×500 mL), and allowed to stand overnight in an additional 500 mL of acetone. The product was collected via filtration and dried under vacuum to give a slightly off color powder. This product (1.2 g) was then added to the larger fraction of wet magnesium bis(peroxydodeconate) from above. This material was divided into two approximately equal portions. One portion was air dried to give 3.7 g white powder (4.69% active O) and the other portion was extruded and allowed to air dry to give 3.3 g extrudate (ca. 2 mm) (4.69% active O). The original fraction containing no alkyl glycosides yielded after air drying 2.0 g white powder (6.00% active O). These three products are referred to hereinafter as MgPLA/AE, MgPLA/A-$E_{extr}$, and MgPLA$_5$, respectively.

EXAMPLE 6

Preparation of Magnesium bis(peroxydodecanoate) Admixed with Sodium Polyacrylate and Linear Alkyl Benzene Sulfonate (LAS)

The procedure outlined in Example 5 was reproduced exactly on a larger scale (4-fold increase). The wet precipitate was divided into three fractions weighing approx. 20 g, 50 g, and 50 g. The first fraction was allowed to air dry giving 8.9 g of a fine white powder (4.53% active O). To one of the larger fractions was added 5 g of sodium polyacrylate (MW=2100). To the second large fraction was added 5 g of a mixture of linear alkane benzene sulfonate (57.4%), sodium polyacrylate (10%), and sodium sulfate (32.6%). Both fractions were allowed to air dry and gave 23.9 g (2.52% active O) and 23.0 g (2.92% active O) respectively.

These three products are referred to hereinafter as MgPLA$_6$, MgPLA/PA, and MgPLA/LAS.

EXAMPLE 7

Preparation of Magnesium bis(peroxyacetate)

A 40% solution of peroxyacetic acid in acetic acid (100 g) was ice cooled and slowly neutralized with a 50% aqueous solution of sodium hydroxide (60 g, 750 mmol). Separately, a solution of magnesium sulfate (60.2 g, 0.50 mol) in water (75 mL) was allowed to react with sodium hydroxide (40 g, 1.0 mol). The peroxy acid solution was added slowly to the resulting magnesium sulfate solution. After 5 min of stirring, the precipitate was filtered (Whatman 40 filter paper) and allowed to air dry for 3 days to give 16.1 g (3.4% based on peroxyacetic acid) of a white solid: Anal. Calcd for $C_4H_{14}MgO_{10}$: O(active), 12.98. Found: O(active), 0.69. After storage under ambient conditions, the product was analyzed to give the following active oxygen percentages: 0.79% (4 days); 0.74% (7 days).

COMPARATIVE EXAMPLE 8

Attempted Preparation of Calcium bis(3-chloroperoxybenzoate)

The procedure described in Example 2 was reproduced exactly except that an equivalent amount of calcium nitrate tetrahydrate was substituted for magnesium sulfate and this was added directly to a solution of 3-chloroperoxybenzoic acid already neutralized with sodium hydroxide (an equivalent amount). (An experiment previous to this one showed that the normal addition described in Example 2 gave no product.) The white precipitate was collected by filtration, washed with water, and dried to give 3.6 g (35% based on calcium nitrate) product: Anal. Calcd for $C_{14}H_8CaCl_2O_6$: O(active), 6.54. Found: O(active), 1.73. After storage under ambient conditions, the product was analyzed to give the following active oxygen percentages: 0.71% (12 days); 0.61% (18 days); 0.42% (33 days).

COMPARATIVE EXAMPLE 9

Preparation of Mercuric bis(3-chloroperoxybenzoate)

3-Chloroperoxybenzoic acid (20.0 g, 0.114 mol, 98%) was added to a solution of sodium hydroxide (2.29 g, 0.573 mol) in 800 mL of water. After the peroxycarboxylic acid had dissolved, this solution was added all at once to a vigorously stirred solution of mercuric chloride (15.5 g, 0.0571 mol) in 800 mL of water. A yellowish solid precipitate formed immediately which was collected by filtration, washed with water (2×500 mL), and vacuum dried 2 h. The solid product was then dried at 40° C. overnight to give 29.9 g (96% based on mercuric chloride) of a slightly wet product: Anal. Calcd for $C_{14}H_8Cl_2HgO_6$: O(active), 5.89: Found: O(active), 4.50. After storage under ambient conditions, the product was analyzed to give the following active oxygen percentages: 4.40% (3 days, still damp); 0.55% (7 days, completely dry).

ANALYTICAL CHARACTERIZATION

The product formed in the process described in Example 1 was analyzed using Fourier Transform Infrared spectroscopy (FT-IR). The spectrum produced showed absorptions at 1714 cm$^{-1}$ and 1680 cm$^{-1}$ (solid state analysis) which are assigned as carbonyl stretching frequencies. Spectra were also obtained for the corresponding 3-chloroperoxybenzoic acid (absorption at 1718 cm$^{-1}$) and magnesium bis(3-chlorobenzoate) (absorptions at 1615 cm$^{-1}$ and 1570 cm$^{-1}$). A portion of the product formed in Example 1 was decomposed by storage for 7 days at 60° C. The spectrum of this material was essentially that of magnesium 3-chlorobenzoate. Analysis in methanol solution resulted in spectra for the product produced in Example 1 (absorption at 1680 cm$^{-1}$) and for 3-chloroperoxybenzoic acid (absorption at 1740 cm$^{-1}$). These results show that the product produced in Example 1 is different from the starting material or the simple magnesium carboxylate salt. Also, the absorption locations for the product from Example 1 are consistent with the values expected for magnesium bis(3-chloroperoxybenzoate)tetrahydrate.

The product formed in Example 3 was also analyzed using FT-IR. The spectrum produced showed an absorption at 1690 cm$^{-1}$ in the solid state with a shoulder at 1705 cm$^{-1}$. The spectrum for peroxydodecanoic acid gave absorptions at 1753 cm$^{-1}$ and 1735 cm$^{-1}$, and for sodium dodecanoate, absorptions occurred at 1560 cm$^{-1}$. Again, the product formed in Example 3 is shown to be unique from the starting material (peroxydodecanoic acid) and the corresponding magnesium carboxylate salt. Also, the absorption locations are consistent with values expected for magnesium bis(peroxydodecanoate) tetrahydrate.

The product formed in Example 1 was also analyzed using $^{13}$C nuclear magnetic resonance (NMR) spectroscopy. In deuterated methanol solution, this product gave signals at 174.55 and 172.60 ppm (downfield from tetramethylsilane) which are assigned to the carbonyl carbon atom. Analysis of 3-chloroperoxybenzoic acid showed a signal at 166.91 (in deuterated chloroform) and 3-chlorobenzoic acid showed a signal at 167.61 (in deuterated methanol). Benzoic acid showed a signal at 169.6 and sodium benzoate showed a signal at 175.4. This last result shows that removal of an acid proton leads to a shift to higher numbers (lower field). The shift from 3-chloroperoxybenzoic acid (166.91) to that of the product formed in Example 1 is consistent with this trend. The second absorption resulting in the spectrum of the product formed in Example 1 is due to magnesium bis(3-chlorobenzoate), the product of the known decomposition of the product from Example 1 in methanol.

These data are consistent with our assignment of the product from Example 1 as magnesium bis(3-chloroperoxybenzoate) tetrahydrate. A reanalysis of this product in deuterated methanol showed again signals at 174.49 and 172.65 ppm. Addition of 4-toluenesulfonic acid to protonate this product resulted in a shift of the signals to 168.05 and 165.88 ppm, features consistent with 3-chlorobenzoic acid and 3-chloroperoxybenzoic acid formed from protonation of magnesium bis(3-chloroperoxybenzoate) tetrahydrate [and the corresponding decomposition product, magnesium bis (3-chlorobenzoate)]. The results show that the product from Example 1 is the same after protonation in solution as the corresponding peroxycarboxylic acid.

STABILITY CHARACTERIZATION

Stability assessments were made by mixing a known measure of active oxygen containing compound into a ten times greater quantity of TIDE ® or other alkaline detergent granular product. The samples were stored for a measured period of time and then the level of active oxygen remaining was determined iodometrically. This process provides data on how well the active oxygen containing compounds survive under ambient storage conditions when admixed with alkaline detergent granular products. This experiment was carried out using 3-chloroperoxybenzoic acid (85% pure) in TIDE ®. The percentage of active oxygen remaining after a specified period of time was 7% (1 day), 4% (2 days), 1% (3 days), and 0% (7 days). The product of Example 1 was used in this experiment and it was found that the percentage of active oxygen remaining after a similar period of time was much higher, i.e., 95% (3 days), 87% (7 days), 68% (25 days). The product from Example 4 was used in this experiment and it was found that the percentage of active oxygen remaining after a similar period of time was even higher, i.e., 100% (36 days). These results show that the magnesium salts of 3-chloroperoxybenzoic acid formed in Example 1 and 4 are much more stable when admixed in an alkaline detergent granular product than is 3-chloroperoxybenzoic acid. For reference, it may be noted that a sample of 3-chloroperoxybenzoic acid was coated with about an equal weight of lauric acid in a fluidized bed after the method described in European Patent Application No. 30,759 and used in the experiment described above. The results showed that the percentage of active oxygen remaining after a similar period of time was not good as the products formed in Examples 1 and 4, i.e., for the coated 3-chloroperoxybenzoic acid, 57% (1 day), 47% (2 days), 30% (6 days), and 5% (37 days). Therefore, it is seen that coating does not confer the desirably high level of stability of the active oxygen admixed with an alkaline detergent granular product.

In a similar fashion the products of Examples 3, 5, and 6 were evaluated for stability. Peroxydodecanoic acid was evaluated for reference. The percentage of active oxygen of peroxydodecanoic acid admixed with TIDE ® remaining after a specified period of time was 53% (4 days), 20% (7 days), and 11% (14 days). The percentage of active oxygen of the MgPLA product of Example 5 remained higher over a similar period of time, i.e., 87% (18 days), 77% (31 days), 67% (41 days). Similarly, the MgPLA/AE product from Example 5 also was analyzed showed 97% (3 days), 92% (7 days), and 84% (14 days). The MgPLA/AE$_{extr.}$ product from Example 5 showed 102% (3 days), 94% (7 days), and 86% (14 days). Many other stability comparisons of this sort were made and in every case the magnesium peroxycarboxylate showed substantially better stability when admixed with an alkaline granular detergent product than the corresponding peroxycarboxylic acid.

The product from the process described in Example 1 was admixed with two inorganic salt mixtures. One was anhydrous magnesium sulfate and sodium carbonate (70:30 weight ratio) and the other was magnesium sulfate heptahydrate and sodium carbonate monohydrate (70:30 weight ratio). The samples were stored at ambient temperatures and analyzed for the remaining active oxygen to ascertain the effects of matrix hydration on the stability of the active oxygen in the product of Example 1. In the anhydrous environment, the level of active oxygen fell to 82% in 7 days and 77% in 14 days whereas in the hydrated environment, essentially no loss of active oxygen was measured over the same period. This result is interpreted to mean that the state of hydration of the matrix in which magnesium bis(3-chloroperoxybenzoate) tetrahydrate is stored is important to the stability of the active oxygen in this, and presumably in related, compounds. The anhydrous environment is thought to reduce the degree of hydration of the product from Example 1 thus reducing the stability of the active oxygen contained therein. The hydrated environment is thought to exert no such dessiciating effect, and the magnesium salt retains its active oxygen.

EXAMPLE 10

A detergent composition in particulate bead form is made by spray drying an aqueous slurry containing about 50% solids composed of Part A ingredients in a conventional counter-current hot air spray drying tower and then sieving the product so that 95% passes through a No. 8 U.S. Standard Series sieve and less than 5% passes through a No. 100 sieve. This material is then admixed with an equal weight of pentasodium tripolyphosphate to give the detergent base. To the detergent base is then added sufficient bleach for the desired end use. In two specific examples, the detergent base was admixed with sufficient amounts of 3-chloroperoxybenzoic acid (CPBA) and, separately magnesium benzoate 3-chloroperoxybenzoate tetrahydrate [Mg(CPBA)] so as to deliver 870 mg $L^{-1}$ of detergent base and 3 ppm active oxygen derived from each of the bleach compounds. Immediately after mixing, each admix was used to wash tea stained swatches. The percent removal of the tea stain is an indication of the effectiveness of the bleach system.

| BASE | Parts in Formula | mg/L$^{-1}$ in Solution |
|---|---|---|
| Part A | | |
| Sodium linear dodecylbenzene sulfonate | 9.2 | 80 |
| Sodium tetradecyldiethoxy sulfate | 4.0 | 35 |
| $C_{12-13}$ polyethoxylate$_{6.5}$ (stripped) | 2.0 | 17 |
| Real Soap (Hyfac) | 1.0 | 9 |
| Pentasodium tripolyphosphate | 20.0 | 174 |
| Sodium silicate (SiO$_2$:NaO = 2.0r) | 3.0 | 26 |
| Water (as hydration) | 5.0 | — |
| Brightener | 1.8 | 16 |
| Calcium Oxide | 0.1 | 1 |
| Sodium sulfate | 12.0 | 104 |
| Part B | | |
| Pentasodium tripolyphosphate | 42.0 | 365 |
| Bleaches | | |
| 3-Chloroperoxybenzoic acid (7.9% active O) | — | 38 |
| Magnesium benzoate 3-chloroperoxybenzoate tetrahydrate (4.0% active O) | — | 75 |

| | Base | + CPBA | + Mg(CPBA) |
|---|---|---|---|
| % Tea stain removal | 53 | 80 | 80 |

Equivalent tea stain removal indicates that the bleaching effect of the magnesium salt is equivalent to that of the acid.

EXAMPLE 11

A detergent composition in particulate bead form is made as in Example 10 by admixing Part A and Part B. Three samples each weighing 7.2 are collected. To each of the two samples is added 3.8 g of magnesium bis(3-chloroperoxybenzoate) tetrahydrate [Mg (CPBA)$_2$] which was determined to contain 6.0% active oxygen. To one of these two samples and also to the third sample is added 1.1 g of enzymes consisting of 0.036 Anson units/gram protease and 990 amylase units/gram amylase. These samples are then added to 7.6 L of water at 100° F. for a detergency experiment.

| BASE | Parts in Formula | mgL$^{-1}$ in Solution |
|---|---|---|
| Part A | | |
| Sodium linear dodecylbenzene sulfonate | 9.2 | 88 |
| Sodium diethoxytetradecanol sulfate | 4.0 | 38 |
| Stripped $C_{12-13}$ polyethoxylated (6.5) alcohol | 2.0 | 19 |
| Pentasodium tripolyphosphate | 20 | 192 |
| Sodium silicate (SiO$_2$:NaO = 2.0r) | 3 | 29 |
| Real Soap (Hyfac) | 1.0 | 10 |
| Brightener | 1.8 | 17 |
| Calcium oxide | 0.1 | 1 |
| Water (as hydration) | 5.3 | — |
| Part B | | |
| Pentasodium tripolyphosphate | 45.0 | 432 |
| Mg(CPBA)$_2$ (6.0% active O) | 8.6 | 83 |
| Protease (Anson units/gram) | 0.036 | — |
| Amylase (amylase units/gram) | 990 | |

In the detergency experiment, three sets of artificially stained swatches were added to the 7.6 L detergent solutions. The solutions were agitated for 10 minutes, rinsed twice, and the test swatches were dried. The swatches were then laid out under suitable lighting conditions and intercompared by three expert graders using the following scale: 0—no difference in the stain removal seen on the compared swatches; 1—thought to be a small difference; 2—certain of a small difference; 3—certain of a large difference; 4—certain of a very large difference. The collected grades were then averaged and normalized to give the data shown:

| Stain Type/Fabric Code | Treatment and Relative Grade | | |
|---|---|---|---|
| | 1. Enzymes | 2. Bleach [Mg(CPBA)$_2$] | Enzymes + Bleach |
| Blood C | 0.0 | −1.2 | −.2 |
| Clay P/C | 0.0 | .2 | .6 |
| Grass P/C | 0.0 | −3.2 | .2 |
| Spaghetti P/C | 0.0 | .3 | .7 |
| Blueberry C | 0.0 | .9 | 1.2 |
| Chocolate Pudding C | 0.0 | −2.6 | −.7 |
| Tea P/C | 0.0 | .9 | .7 |

C = cotton fabric
P/C = polyester and cotton (65/35) fabric

The comparative results show that the benefit of protease enzymes on blood and grass stains is not reduced by Mg(CPBA)$_2$ bleach. The benefit of amylase enzymes on chocolate pudding is marginally reduced by Mg(CPBA)$_2$ bleach. And the benefit of Mg(CPBA)$_2$ bleach on spaghetti, tea, and blueberry stains is not impaired by the presence of the enzymes.

Similar tests conducted with magnesium monoperoxyphthalate hexahydrate showed that the enzyme stain removal function was significantly impaired in this test.

EXAMPLE 12

A detergent composition in particulate bead form is made by spray drying an aqueous slurry containing about 50% solids (shown in the table below) in a conventional counter-current hot air spray drying tower and then sieving the product so that over 95% passes through a No. 8 U.S. Standard Series sieve and less than 5% passes through a No. 100 sieve. The magnesium bis(3-chloroperoxybenzoate) tetrahydrate from Example 3 is post added and blended into the detergent composition to a 5 weight % level. In variations of the experiment, the products from Examples 1, 2, 4–9 can be substituted at a similar level.

| | Parts in Formula | mgL$^{-1}$ in Solution |
|---|---|---|
| Sodium linear tridecylbenzene sulfonate | 7.5 | 113 |
| Sodium tetradecanol sulfate | 10.0 | 150 |
| Pentasodium tripolyphosphate | 32.6 | 490 |
| Sodium silicate (SiO$_2$:Na$_2$O = 2.0r) | 3.0 | 45 |
| Sodium carbonate | 3.0 | 45 |
| Sodium sulfate | 32.7 | 491 |
| Water (as hydration) | 5.0 | 75 |
| Mg (CPBA)$_2$ | 5.0 | 75 |
| Brightener | 0.2 | 3 |
| Sodium carboxymethyl cellulose | 1.0 | 15 |
| Protease (anson units/per gram) | 0.04 | — |

This composition has excellent detergent and bleaching properties.

EXAMPLE 13

A laundry bleach additive product in particulate bead form is prepared by spray drying an aqueous slurry containing about 50% solids composed of Part A ingredients in a conventional counter-current hot air spray drying tower and then sieving the product as described in Example 10. The material is then admixed with a four-fold excess of Part B ingredients to give the laundry bleach additive product.

| | Parts in Total Formula | mgL$^{-1}$ in Solution |
|---|---|---|
| Part A | | |
| Sodium linear tridecylbenzene sulfonate | 5.5 | 50 |
| Sodium sulfate | 11 | 100 |
| Sodium polyacrylate (M.W. = 1500) | .6 | 5 |
| Part B | | |
| Mg (CPBA)$_2$ (6.0% active O) | 18 | 160 |
| The enzymes of Example 11 | 2.2 | 20 |
| Sodium bicarbonate | 11 | 100 |
| Brightener | .7 | 6 |
| Diethylenetriaminepentaacetate | 1.1 | 10 |
| Sodium sulfate | 44 | 400 |
| Water (as hydration) | 5.4 | 49 |

When laundry is washed in an aqueous solution containing 0.90 gL$^{-1}$ of this composition, excellent stain removal and whiteness are achieved. In variations of this example, pentasodium tripolyphosphate can be substituted for all or part of the sodium sulfate in Part B. Also, magnesium 1,12-dodecanediperoxycarboxylate tetrahydrate can be substituted for the Mg(CPBA)$_2$ in Part B.

EXAMPLE 14

A scouring cleanser is prepared by admixing the ingredients outlined below. This formula shows excellent performance against stains on porcelain or stainless steel sinks and countertops. In variations of this example, other magnesium bis(peroxycarboxylate) tetrahydrates may be employed.

| | |
|---|---|
| Mg (CPBA)$_2$ | 15 parts |
| Sodium linear tridecylbenzene sulfonate | 3 |
| Pentasodium tripolyphosphate | 3 |
| Silex (finely divided silica) | 79 |

EXAMPLE 15

An ointment for the control of acne is prepared by admixing the ingredients shown below. When applied topically, the ointment is effective in reducing the spread of acne.

| | |
|---|---|
| Mg (CPBA)$_2$ | 2 parts |
| Astringent | 5 |
| Nonoily base (e.g. polypropylene glycol, M.W. 15,000) | 93 |

EXAMPLE 16

A denture cleanser is prepared by admixing the ingredients shown below. When soiled dentures are soaked in an aqueous solution containing the admix, effective stain removal and whitening is obtained.

| | |
|---|---|
| Mg (CPBA)$_2$ | 10 parts |
| Sodium bicarbonate | 30 |
| Tetrasodium Ethylenediaminetetraacetate | 5 |
| Sodium sulfate | 50 |
| Ultramarine blue dye | 0.01 |
| Water (as hydration) | 5 |

EXAMPLE 17

An automatic dishwashing detergent in particulate bead form is made by admixing the following ingredients:

| | |
|---|---|
| Pentasodium tripolyphasphate | 45 parts |
| Sodium silicate (SiO$_2$:Na$_2$O = 2.8) | 14 |
| Wyandotte's Pluradot ® HA-430 surfactant | 3 |
| Water (as hydration) | 27 |
| Mg (CPBA)$_2$ | 10 |

In variations, the magnesium peroxycarboxylate products from Examples 1, 2, 4–9 can be substituted at similar levels.

EXAMPLE 18

A toilet bowl cleanser in particulate bead form is prepared by admixing the following ingredients. When added to a toilet bowl followed by scrubbing and/or a period of time, effective cleansing and sanitizing of the surface occurs.

| | |
|---|---|
| Mg (CPBA)$_2$ | 20 parts |
| Pentasodium tripolyphosphate | 30 |
| Sodium tridecylbenzenesulfonate | 3 |
| Sodium polyacrylate (M.W. = 1500) | 1 |
| Diethylenetriaminepentaacetate | 1 |
| Sodium sulfate | 40 |
| Water (as hydration) | 5 |

EXAMPLE 19

A detergent composition in particulate bead form is prepared as in Example 10 using the composition detailed below.

| | Parts in Total Formula | mgL$^{-1}$ in Solution |
|---|---|---|
| Part A | | |
| Sodium aluminosilicate (Zeolite A, 1–3μ) | 24.0 | 360 |
| Sodium carbonate | 10.0 | 150 |
| Sodium polyacrylate (MW = 10,000) | 3.0 | 45 |
| Sodium tridecylbenzene sulfonate | 10.0 | 150 |
| Sodium tetradecyldiethoxy sulfate | 10.0 | 150 |
| Sodium silicate (SiO$_2$:Na$_2$O = 2.0r) | 3.0 | 45 |
| Water (as hydration) | 5.0 | 75 |
| Brightener | 0.2 | 3 |
| Sodium sulfate | 29.8 | 447 |
| Part B | | |
| Mg (CPBA)$_2$ (6.0% active O) | 5.0 | 75 |
| Protease (Anson units/gram) | 0.04 | — |

This composition provides effective bleaching and detergency without containing phosphorus or boron.

EXAMPLE 20

Larger Scale Production of Magnesium Bis(3-Chloroperoxybenzoate) Tetrahydrate An aqueous sodium hydroxide solution (1.22 M, 1.82 L, 2.21 moles NaOH) was added with stirring to an aqueous magnesium sulfate solution (0.367 M, 3.0 L, 1.103 moles MgSO$_4$) in a 12-L round-bottomed glass reactor fitted with an overhead stirrer. After 5 min, 3-chloroperoxybenzoic acid (85%, 375 g, 0.36 moles acid, 1.85 moles peroxyacid) in 4.82 L of ethyl acetate was added all at once. After 30 min., the solids were collected by filtration, washed (ethyl acetate and water), and allowed to dry, giving 442.4 g (91.3% based on MgSO$_4$), 86% (active oxygen retained) of fine white powder: Anal. Calcd: O(active) 6.18. Found: O(active) 5.76.

EXAMPLE 21

Preparation of Magnesium Diperoxydodecanedioate Tetrahydrate

A solution of magnesium sulfate (6.7 g, 56 mmol) in water (120 ML) was combined with a solution of sodium hydroxide (4.4 g, 110 mmol) in 120 mL to give a colloidal suspension of magnesium hydroxide. Diperoxydodecanedioc acid (94.6%, 30.9 g, 111 mmol) in ethyl acetate (240 mL) was added all at once with vigorous stirring. After 15 min., the wet precipitate was collected by filtration, washed with water (ca. 200 mL), and allowed to dry overnight giving 18.3 g (53% based on Mg$^{2+}$, 31% active oxygen retained) of a fine, colorless powder: Anal. calcd: O(active), 10.3. Found: O(active), 6.02. This material is found to bleach equivalent to the starting peroxyacid at equal active oxygen levels.

EXAMPLE 22

Alternate Preparation of Magnesium Diperoxydodecanedioate Tetrahydrate

The procedure of Example 21 was reproduced exactly except that the level of diperoxydodecanedioc acid was reduced by half. This process gave a 70% yield of fine colorless powder: Anal. Calcd: O(active), 10.3. Found: O(active), 4.33.

EXAMPLE 23

Alternate Preparation of Magnesium bis(3-Chloroperoxybenzoate) Tetrahydrate Using t-butyl Alcohol.

The procedure of Example 2 was repeated exactly except that t-butyl alcohol was used in place of ethyl acetate. This gave a 70% yield of the desired product having 6.55% active oxygen.

EXAMPLE 24

A laundry bleach additive contained in a pouch as disclosed in U.S. Pat. No. 4,374,035, Bossu (July 13, 1981), incorporated herein by reference, is prepared using magnesium peroxycarboxylates such as Mg(CPBA)$_2$. A bleach composition consisting of the ingredients outlined below is placed in a 76 mm×230 mm piece of polyester nonwoven substrate having a density of 60 g/m$^2$ which is then folded in half and heat sealed on three sides to form a pouch 76 mm×115 mm. The nonwoven substrate may be Sontara ® sold by DuPont.

| Composition per pouch (grams) | |
|---|---|
| Mg (CPBA)$_2$ | 10 |
| Na$_2$SO$_4$.7 H$_2$O | 6 |
| Sodium dodecyl sulfate | 2.4 |
| Benzoic acid | 3 |

What is claimed is:

1. Stable solid organic oxidizing compound comprising the group

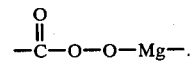

2. The compound of claim 1 in hydrated form.

3. Stable magnesium peroxycarboxylate of the formula:

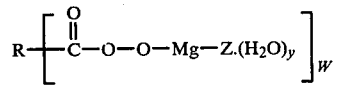

wherein R is H, O$^-$, or an organic moiety, Z is a compatible counterion and W is a number from about 1 to about 100.

4. The compound of claim 3 wherein R is selected from the group consisting of H, a linear or branched alkyl group, an aryl group, an alkylaryl group, an aromatic heterocyclic group, a polyarylene group consisting of 2 or more annelated benzenoid rings, and mixtures thereof containing up to about 18 carbon atoms and said R group being optionally substituted with halogen atoms, or sulfonate, nitro, carboxylate, percarboxyl, carboxyl, C$_{1-5}$ alkyl, alcohol, hydroxy, trifluoromethyl, methoxy carbonyl, amino carbonyl, C$_{1-5}$ alkoxy, hydroxy, sulfonyl, aryl, ammonium and substituted ammonium, sulfone, amine oxide, amide, ester or sulfate groups, or mixtures thereof.

5. The compound of claim 4 wherein R is selected from the group consisting of an alkyl group contaiing from 8 to about 18 carbon atoms, an aryl group optionally substituted with up to 2 groups selected from the group consisting of chloro, bromo, or fluoro, atoms, sulfonate groups, nitro groups and alkyl groups containing from 1 to about 4 carbon atoms, and mixtures thereof.

6. The compound of claim 5 wherein R is a monochlorophenyl group.

7. The compound of claim 5 wherein R is an alkyl group containing from about 12 to about 18 carbon atoms.

8. The compound of claim 3 wherein R is a polymer and W is a number from about 5 to about 100.

9. The compound of claim 3 wherein Z is selected from the group consisting of:

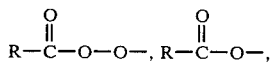

sulfate, sulfonate, chloride, bromide, iodide and nitrate anions and mixtures thereof, and each R group can be different.

10. The compound of claim 9 wherein Z has the formula:

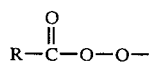

and each R can be different.

11. The compound of claim 10 wherein R is selected from the group consisting of H, a linear or branched alkyl group, an aryl group, an alkylaryl group, an aromatic heterocyclic group, a polyarylene group consisting of 2 or more annelated benzenoid rings, and mixtures thereof containing up to about 18 carbon atoms and said R group being optionally substituted with halogen atoms, or sulfonate, nitro, carboxylate, percarboxyl, carboxyl, $C_{1-5}$ alkyl, alcohol, hydroxy, trifluoromethyl, methoxy carbonyl, amino carbonyl, $C_{1-5}$ alkoxy, hydroxy, sulfonyl, aryl, sulfone, amine oxide, amide, ester or sulfate groups, or mixtures thereof.

12. The compound of claim 11 wherein R is selected from the group consisting of an alkyl group containing from 8 to about 18 carbon atoms, an aryl group optionally substituted with up to 2 groups selected from the group consisting of chloro, bromo, or fluoro atoms, sulfonate groups, nitro groups and alkyl groups containing from 1 to about 4 carbon atoms, and mixtures thereof.

13. The compound of claim 12 wherein R is a monochlorophenyl group.

14. The compound of claim 12 wherein R is an alkyl group containing from about 12 to about 18 carbon atoms.

15. The compound of claim 3 in hydrated form containing from about 1 to about 6 moles of water for each mole of magnesium.

16. A detergent composition comprising an organic detergent surfactant and an effective amount of the compound of claim 3.

17. The composition of claim 16 wherein R is selected from the group consisting of H, a linear branched alkyl group, an aryl group, an alkylaryl group, an aromatic heterocyclic group, a polyarylene group consisting of 2 or more annelated benzenoid rings, and mixtures thereof containing up to about 18 carbon atoms and said R group being optionally substituted with halogen, sulfonate, nitro, carboxylate, percarboxyl, carboxyl, $C_{1-5}$ alkyl, alcohol, hydroxy, trifluoromethyl, methoxy carbonyl, amino carbonyl, $C_{1-5}$ alkoxy, hydroxy, sulfonyl, aryl, ammonium and substituted ammonium, sulfone, amine oxide, amide, ester or sulfate groups, or mixtures thereof.

18. The composition of claim 17 wherein R is selected from the group consisting of an alkyl group containing from 1 to about 18 carbon atoms, an aryl group optionally substituted with up to 2 groups selected from the group consisting of halogen atoms, sulfonate groups, nitro groups and alkyl groups containing from 1 to about 4 carbon atoms, and mixtures thereof.

19. The composition of claim 18 wherein R is a monochlorophenyl group.

20. The composition of claim 19 additionally containing an effective amount of an enzyme selected from the group consisting of detergent proteases, detergent amylases and mixtures thereof.

* * * * *